United States Patent [19]

Kaestle

[11] Patent Number: 5,299,120
[45] Date of Patent: * Mar. 29, 1994

[54] METHOD FOR DIGITALLY PROCESSING SIGNALS CONTAINING INFORMATION REGARDING ARTERIAL BLOOD FLOW

[75] Inventor: Siegfried Kaestle, Nufringen, Fed. Rep. of Germany

[73] Assignee: Hewlett-Packard Company, Palo Alto, Calif.

[*] Notice: The portion of the term of this patent subsequent to Jan. 29, 2010 has been disclaimed.

[21] Appl. No.: 408,001

[22] Filed: Sep. 15, 1989

[51] Int. Cl.⁵ .............................................. G06F 15/42
[52] U.S. Cl. ................................. 364/413.09; 128/666
[58] Field of Search ...................... 364/413.09, 413.03; 356/41; 128/664, 633, 666

[56] References Cited

U.S. PATENT DOCUMENTS

| | | | |
|---|---|---|---|
| 4,313,445 | 2/1982 | Georgi | 128/680 |
| 4,418,700 | 12/1983 | Warner | 128/694 |
| 4,653,498 | 3/1987 | New, Jr. et al. | 128/633 |
| 4,800,495 | 1/1989 | Smith | 364/413.03 |
| 4,802,486 | 2/1989 | Goodman et al. | 128/633 |
| 4,859,056 | 8/1989 | Prosser et al. | 356/41 |
| 4,911,167 | 3/1990 | Corenman et al. | 128/633 |
| 4,928,692 | 5/1990 | Goodman et al. | 128/633 |

Primary Examiner—Gail O. Hayes

[57] ABSTRACT

A method for digitally processing signals containing information regarding arterial blood flow in a living body is disclosed enabling a more accurate determination of the oxygen saturation. The method comprises the steps of identifying a first edge based on a first derivation of the signal, disregarding same if it does not fulfill certain criteria, determining a window based on said identified first edge, identifying the second edge falling within said window, disregarding same if it does not fulfill certain criteria, and replacing the second edge by the first before repeated these steps.

3 Claims, 10 Drawing Sheets

METHOD FOR DIGITALLY PROCESSING SIGNALS CONTAINING INFORMATION REGARDING ARTERIAL BLOOD FLOW

FIELD OF THE INVENTION

The present invention relates to non-invasive pulse oximetry and specifically to an improved method for digitally processing the signals generated by an oximeter.

BACKGROUND OF THE INVENTION

As is known, the fraction of hemoglobin in arterial blood which is in the form of oxygenated Hb and which is often referred to as the oxygen saturation of blood SaO2, can be measured by a photo-electric measuring device known as oximeter. As will be explained later on in more detail, the saturation of oxyhemoglobin (hemoglobin combined with oxygen) in arterial blood in the tissue of a living body can be detected by means of light of at least two different wavelengths passing through or reflecting from the tissue so as to be modulated by the pulsatile blood flow therein. The reason for the variation of the transmission or reflection of the light through the blood in that the absorption coefficient of oxyhemoglobin is different from that of deoxygenated hemoglobin for different wavelengths of light. Thus, the measurement of the amount of light passing through or reflected from a member of the body having a pulsatile blood flow therein can be used for indicating the saturation of hemoglobin in the blood. As is also known in the art, fixed absorbers of the tissue reduce the amount of light passing through or being reflected from the body by an essentially constant amount which can be regarded as a DC component. A pulsatile component or AC component of the light at different wavelengths passing through or reflecting from the body is primarily caused by the effect the changing arterial blood volume within the member of the body has on the passing or reflected light.

Consequently, most of the prior art oximeters eliminate the DC component from the signals analysed and only utilize the pulsatile component for the calculation of the oxyhemoglobin saturation. For example, U.S. Pat. No. 4,167,331 (Nielsen) discloses a technique of determining the pulse rate and arterial oxygen saturation by means of a three-wavelengths absorbence oximetry, where the DC components of the respective signals are suppressed or eliminated by bandpass filters. The bandpass filtering of the signal results in a signal distortion negatively affecting the accuracy in determination of the pulse rate and the oxygen saturation. This prior art technique is also involved with another problem resulting from the fact that this technique starts from the assumption that the AC component is exclusively caused by a change in the volume of the blood. However, this assumption underlying the prior art oximeter as exemplified by U.S. Pat. No. 4,167,331 appears to be too rough as the following factors may influence the oximetry signals: venouse pulsation caused by an excessive contact pressure force of the sensor, the influences of electrical noises caused by radio frequency apparatus for the surgery, optical interferences generated by adjacent light sources of pulsatile character, misplacements of the sensor itself at the measuring position as well as artifacts due to the patient's motions.

Although most of the prior art oximeters are equipped with averaging circuits for averaging measured values concerning the oxygen saturation and the pulse frequency over a period of seconds, or at least a plurality of pulses before generating a display of these values, noisy peaks of the above-indicated types nevertheless have a certain negative influence on the accuracy which can be achieved with this prior art oximeter.

For enhancing the accuracy by particularly processing the signals used in oximetry, EP-262,778-A1 (Physio-Control Corporation) discloses a method of processing oximetry signals by firstly searching for a sustained positive sloping region of the signal, determining the respective times before and after the occurence of a slope reversal, searching for a maximum which is identified as a positive peak after a first positive slope and searching for a negative peak after occurrence of a negative sloping region. For improving the accuracy, signals failing to comply with predetermined requirements are rejected. For example, pulse amplitudes not satisfying a predetermined amplitude selection criterion are rejected. The rejection criterion may also include a systolic interval template defining an allowable systolic interval range for defining a time interval between positive and negative peaks. Although this prior art oximetry method appears to be suitable for enhancing the measuring accuracy by eliminating or suppressing the influence of certain noisy signals, it is not suitable for eliminating an effect on the measurement accuracy by motional artifacts or dicrotic pulses.

SUMMARY OF THE INVENTION

It is an object of the invention to provide an improved method for digitally processing signals in the field of oximetry having an improved accuracy in determining the degree of saturation of oxyhemoglobin and/or the pulse frequency.

It is also an object of the invention to provide an improved oximetry method including digitally processing the signal for determining oxyhemoglobin saturation of the blood which is not negatively affected by motional artifacts or by dicrotic pulses.

This object is achieved in accordance with the present invention by a method for digitally processing signals containing information regarding arterial blood flow in a living body, comprising the steps of:

identifying a first systolic edge of the signal based on at least one feature of the edge of the signal including at least the maximum absolute value of the first derivative, disregarding the identified first systolic edge in case certain criteria concerning the first edge are not fulfilled, and again searching for another first systolic edge, determining a window within which the signal is examined as to an expected second systolic edge, said window being defined based on values of said identified and accepted first systolic edge, identifying the second systolic edge of the signal, in case certain criteria concerning the second edge are not fulfilled, disregarding the identified second systolic edge and returning to the step of searching for another first or second edge, replacing certain values of characteristics of the first systolic edge by those of the second and returning to the step of defining the window based on the values of the actual edge.

BRIEF DESCRIPTION OF THE DRAWINGS

The accompanying drawings illustrate a complete embodiment of the invention according to the best mode of implementation so far devised for the practical application of the principles thereof, and in which.

DESCRIPTION OF THE PREFERRED EMBODIMENT OF THE INVENTION

Figure 1:
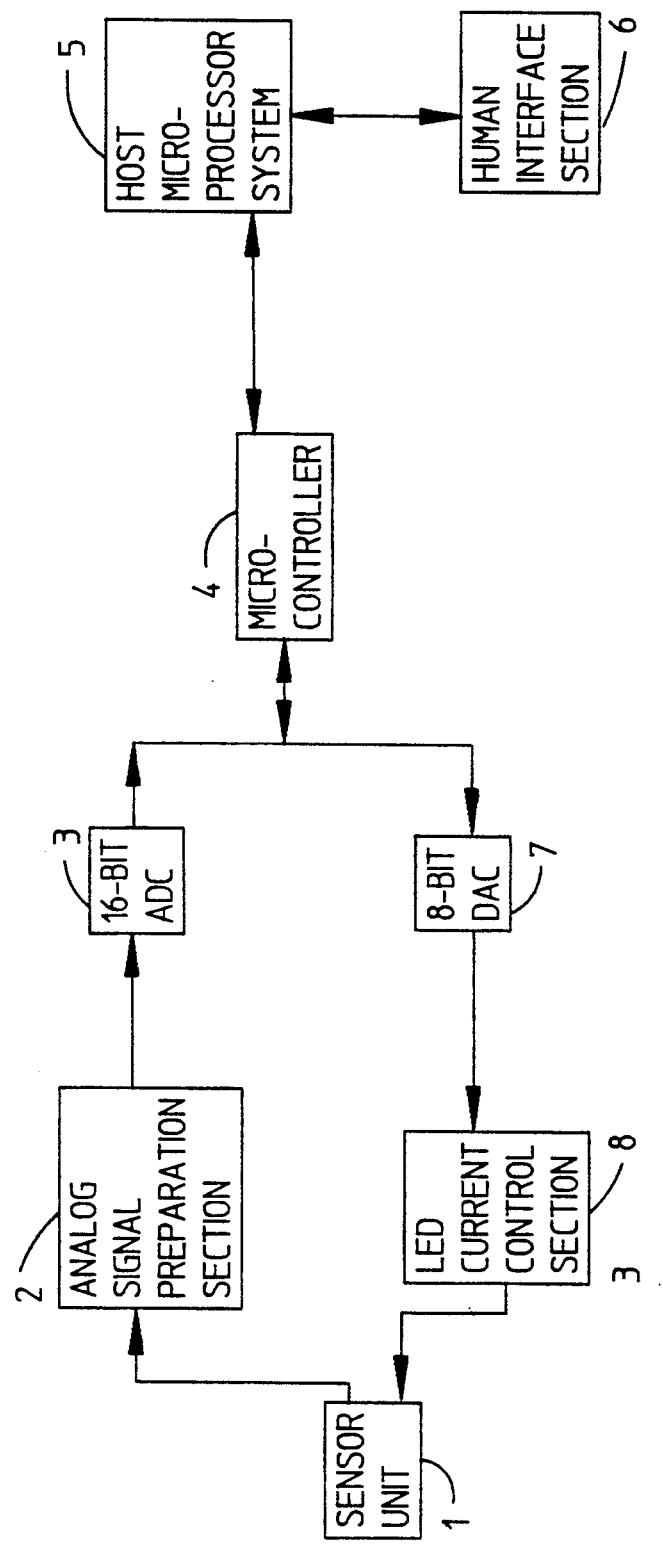
FIG. 1 is a block diagram of an oximeter according to the invention.

As depicted in FIG. 1, an oximeter comprises a sensor unit 1, an analog signal preparation section 2, an analog-digital-converter ADC having a high resolution of e.g. 16 bit, to which a microcontroller 4 is connected which in turn communicates with a host microprocessor system 5 to which a human interface section 6 is connected which may comprise a display and a keyboard. The microcontroller 4 is further connected to an 8-bit digital-to-analog-converter DAC 7 for generating analog control signals, which are fed to a subsequent LED current control section 8 which in turn generates the necessary driver currents for driving the sensor unit 1.

The sensor units may have the usual design of sensor unit of oximeters and may comprise two LEDs suitable for emitting light at different frequences which may be in the range of red light having a wavelength of 650 nm and in the range of infra-red light having a wavelength of 1000 nm.

The microcontroller 4 causes the generation of supply driving currents within the sensor unit 1 in a time-multiplexed mode having a frame frequency of 375 Hz activating the LEDs subsequently to each other for a respective period of time of 600 microseconds. A dark period serving for the measurement of the light of the environment follows to the periods of activation of the respective LEDs.

Thus, the output signals of the sensors are generated in a time-multiplexed manner with regard to the respective wavelengths of the LEDs including the dark period mentioned above. The analog-digital-conversion as carried out by ADC 3 requires a high resolution of the signal recognition for enabling the detection of a weak pulsation having an amplitude of smaller than 1% of the DC-component of the signal.

Figure 2:
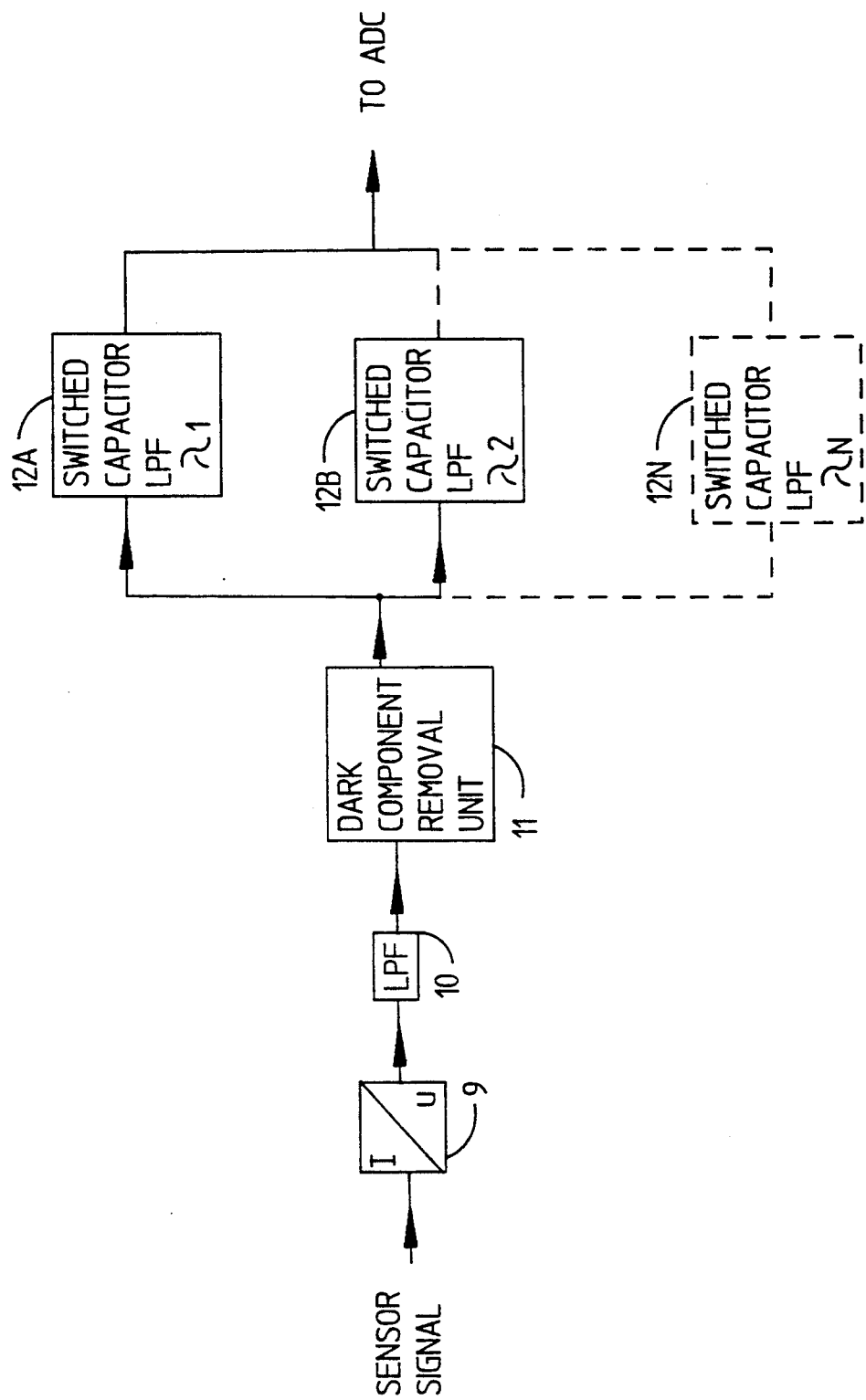
FIG. 2 is a block diagram of an analog signal preparation section shown in FIG. 1.

As shown in FIG. 2, which is a more detailed representation of the analog signal preparation section 2 indicated in FIG. 1, the sensor signal is fed to a current-voltage-converter 9, which is connected to a low pass filter 10 for limiting the band width of the signal so as to eliminate noisy signals in the radio frequency range as generated by radio frequent devices for the surgery which operate at levels of several hundred volts. Subsequently, a dark component removal unit 11 conducts a removal of the dark component as detected during the respective dark period mentioned above. Thereinafter, the signal is fed to switched capacitor low pass filters 12A, 12B . . . 12N for conducting a filtering of the signal for each wavelength lambda 1, lambda 2, . . . lambda N. The switched capacitor low pass filters 12A to 12N eliminate undesired noisy components and limit the bandwidth of the resulting coarse waveforms to the physiologically relevant bandwidth of an arterial pulse in the range of 0 to 10 Hz. This limitation of the bandwidths further serves for complying with the Nyquist requirements for the subsequent sampling of the signal and prevents aliasing effects which are caused, for example, by noisy interferences of the light of the environment having the supply line frequency.

Figure 3:
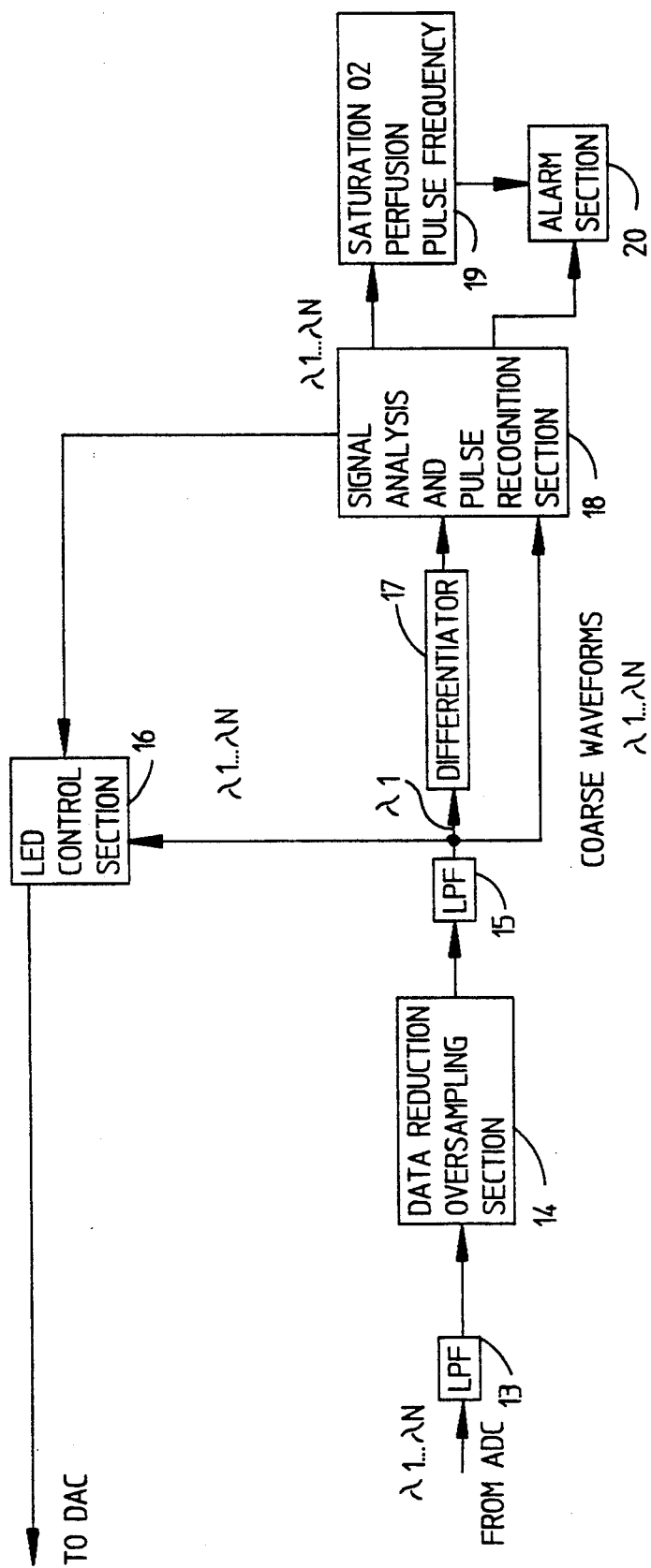
FIG. 3 is a block diagram of a digital signal processing section included in the microcontroller shown at FIG. 1.

The subsequent additional digital multi-pole low pass filter 13 (FIG. 3) serves for essentially suppressing noises at frequencies which do not fail within the physiological band widths. Thus, the signal-to-noise-ratio is further enhanced.

The above-mentioned sampling of the signal is conducted by the data reduction (oversampling) section 14 which reduces the sample rate to 125 Hz. The output of data reduction section 14 is connected to a further digital multi-pole low pass filter 15 essentially corresponding to low pass filter 13.

The cut-off frequency of these filters 13, 15 can be controlled depending on the pulse frequency of the patient which results in a minimal distortion of the useful signal whilst effectively suppressing noises outside the band width.

The identical operation of these digital low pass filters 13, 15 for each wavelength guarantees that the signal contents for each wavelength are equally amended. Thus, all requirements for a subsequent calculation of the oxygen saturation with a high accuracy are complied with.

The coarse wave forms for the respective wavelengths are fed to an LED control section 16 serving to control the driving currents of the LEDs so that an optimal signal level at the input side of ADC 3 for effecting the analog-digital-conversion is achieved.

The coarse wave form of a specific wave length lambda 1 is fed to a differentiator 17 for generating a first derivative of the signal required for the later signal analysis which is carried out by the signal analysis and pulse recognition section 18. The mode of operation of the signal analysis and pulse recognition section which is implemented by a software routine will be described hereinafter in more detail with reference to FIGS. 5 to 8.

The main purpose of the signal analysis and pulse recognition section 18 is to identify relevant wave form points, to extract same and to decide whether the identified or recognized pulse is an arterial pulse or a noise, for example an artifact. The analysis of the respective signals is a main aspect of the present invention, whilst the determination of the oxygen saturation on the basis of detected maximum values and minimum values of the signals at different wavelengths is known per se in the art. For the sake of completeness of disclosure, reference is made to EP-A-262 778 (Smith) disclosing in detail the determination of the pulse frequency and the saturation of oxyhemoglobin based on detected maximum and minimum values at the beginning and end of a systolic edge of a signal for different wavelengths of the light.

As will be described in more detail hereinafter, the determined oxygen saturation, the perfusion and the pulse frequency are displayed by a display unit 19. Under certain conditions such as excessive appearances of artifacts or a missing pulsatile character of the coarse wave form, an alarm section 20 is actuated.

Figure 4:
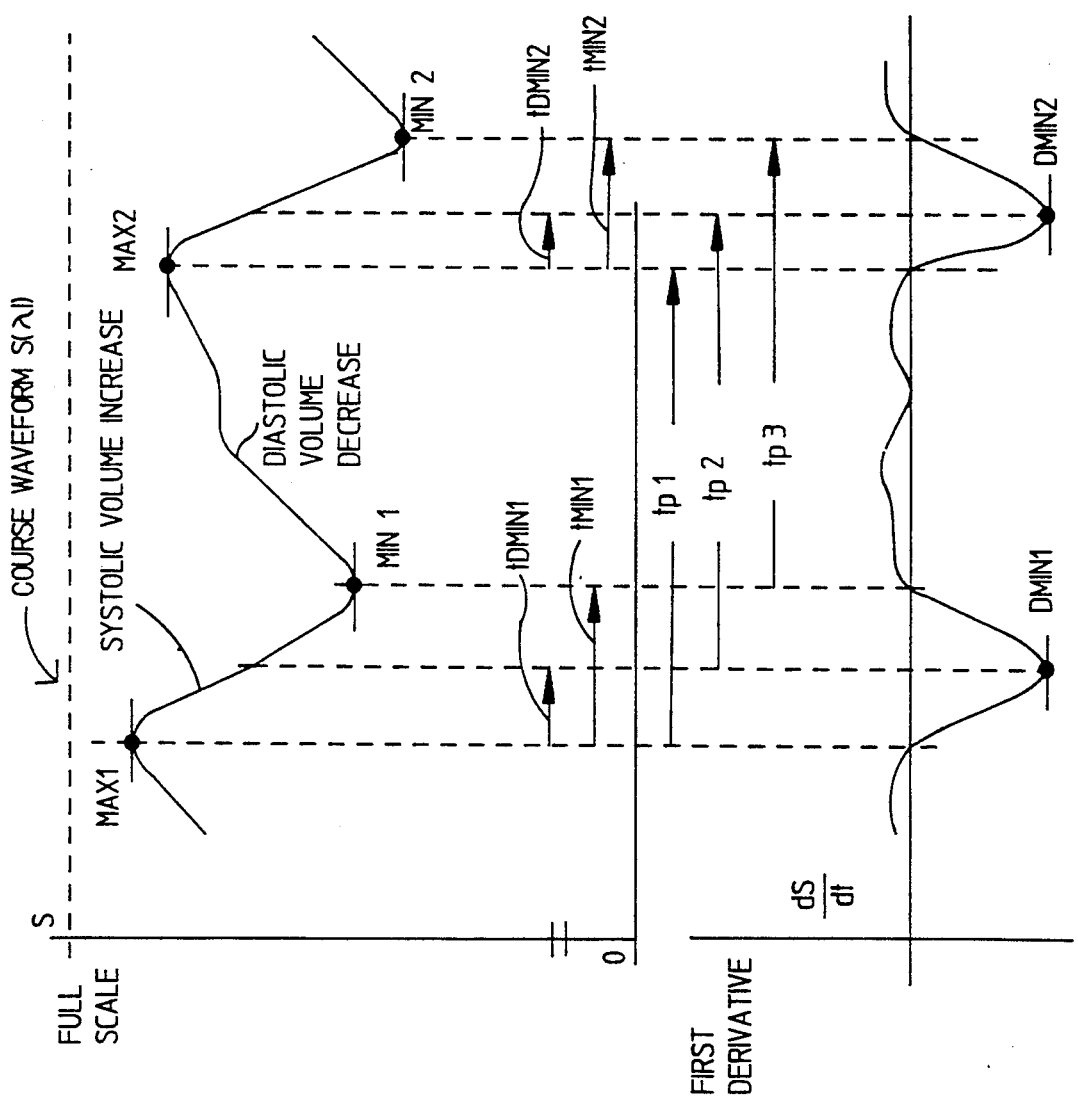
FIG. 4 depicts the coarse wave form of the sensor signal at a certain wavelength of the light as well as the first derivative thereof.

FIG. 4 shows the coarse waveform of a signal for a predetermined wavelength number 1 and the first derivative thereof as generated by the differentiator 17. The coarse waveform essentially comprises a first decreasing edge between a first maximum MAX 1 and first minimum MIN 1 corresponding to a systolic volume increase, a first increasing edge corresponding to a diastolic volume decrease between said minimum MIN 1 and a second maximum MAX 2, and a second decreasing edge between said maximum MAX 2 and the next minimum MIN 2. The start of the respective systolic edge is defined as being the reference time t=0. The time of occurrence of the minimum MIN1, MIN2 is defined as tMIN1, tMIN2. The time of occurrence of the absolute maximum value of the first derivative DMIN1, DMIN2 is defined as being tDMIN1, tDMIN2.

Figure 5:
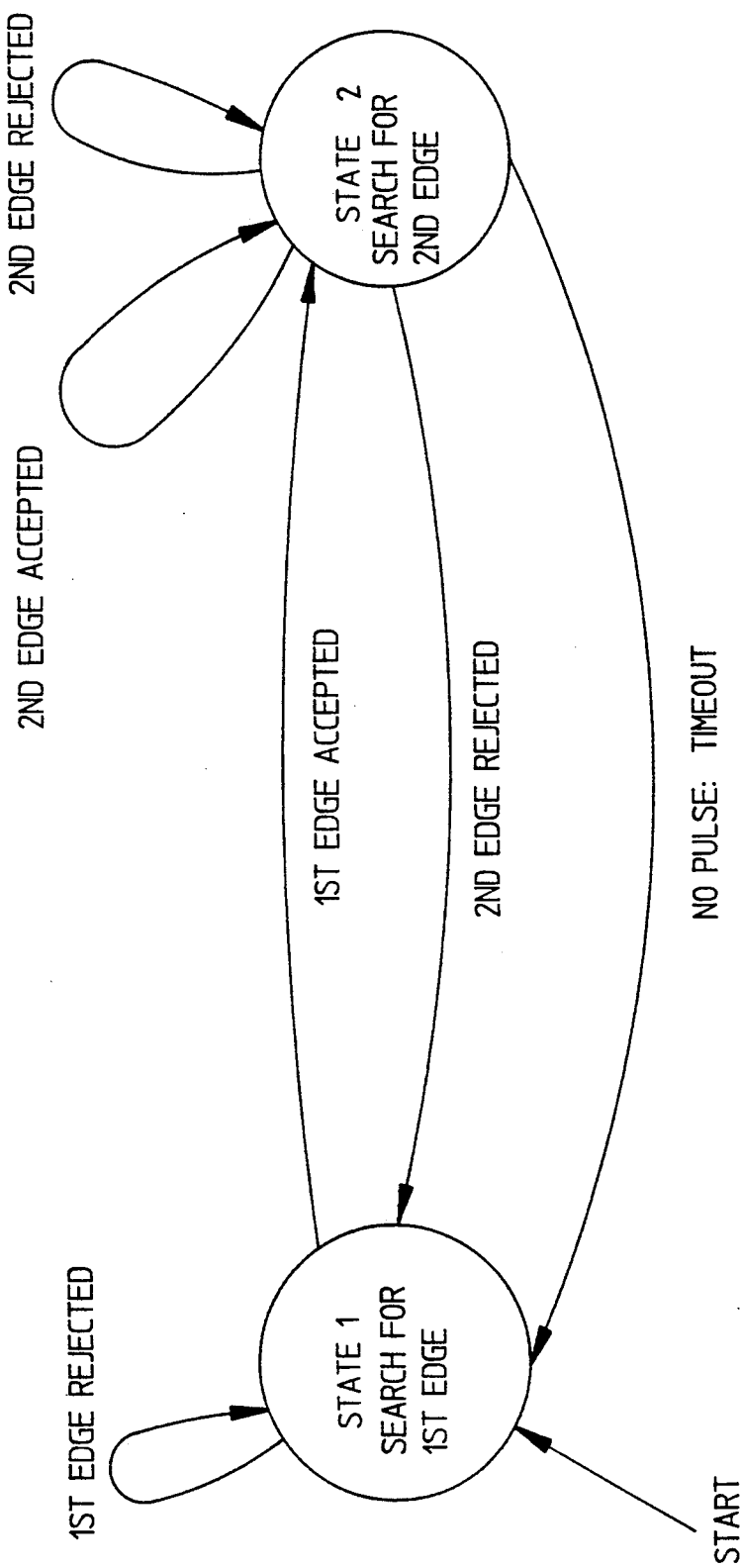
FIG. 5 depicts a state diagram of the signal processing software in accordance with the present invention.
Figure 6:
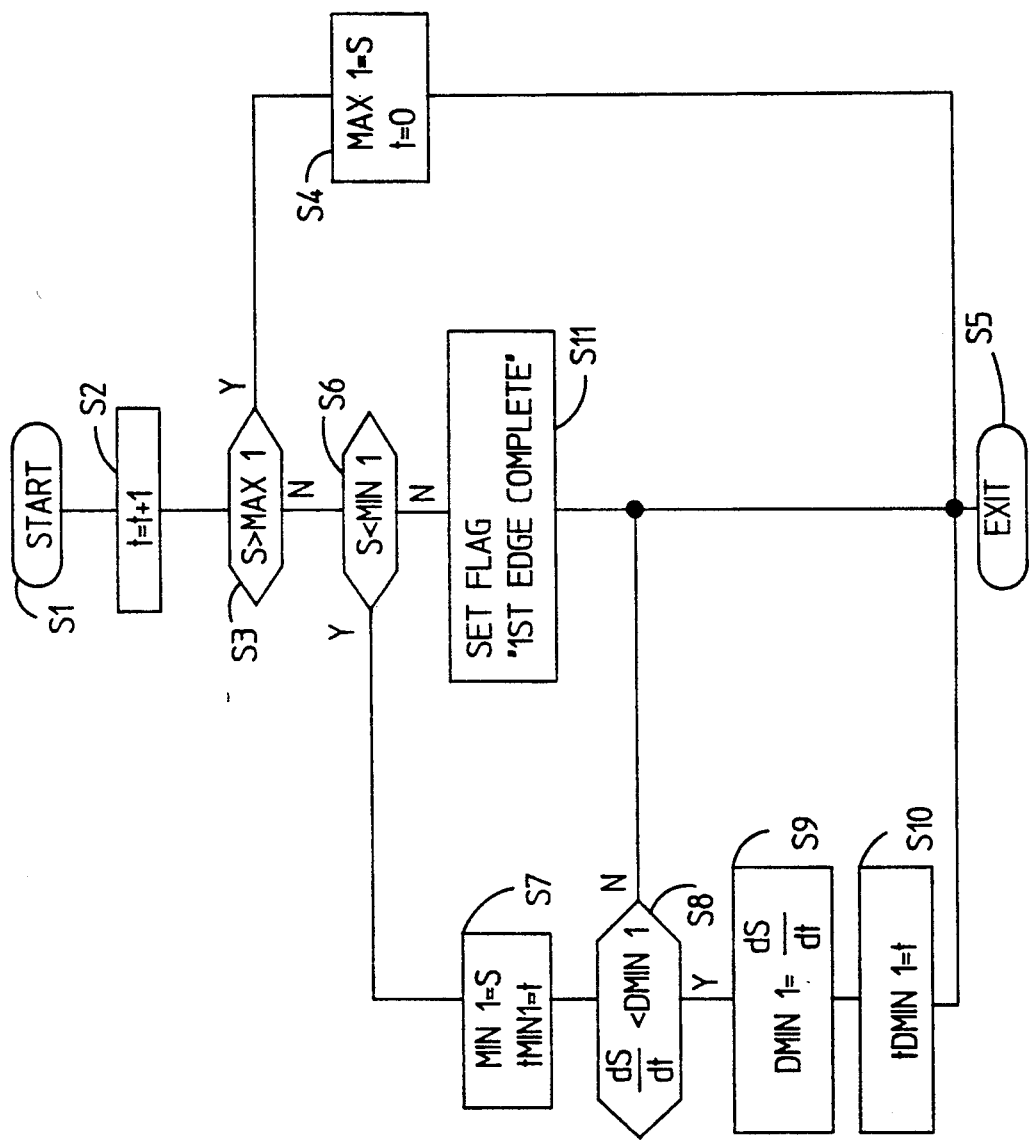
FIG. 6 depicts a flow diagram concerning the search for a first edge of the signal.

As depicted in FIG. 5, the method of digitally processing signals implemented by the software, which will be described with reference to FIGS. 6 to 8, has two different states, as will be appreciated by men skilled in the present field when considering the state diagram in accordance with FIG. 5. After starting the program, it remains in state 1 searching for a first edge as long as respective first edges are rejected. When accepting a first edge, the program enters into a second state (state 2) in which it searches for a second edge. As long as further edges are accepted as new (second) edges, the program remains in state 2. If a timeout is reached before the occurrence of a second edge, it switches back to the first state. Depending on details which will be explained later, the rejection of a second edge may either lead to remaining in the second state or to switching back to the first one. FIG. 6 discloses a firt part of a software routine essentially corresponding to state 1. After starting the software routine at step S1, the time basis is incremented at step S2. At step S3 the actual signal is compared to a predetermined maximum MAX1. If S exceeds MAX1, MAX1 is updated to equal S and the time basis is set to be zero at step S4. Then the program goes to the exit S5. At S6, it is examined whether S is smaller than the minimum value MIN1. If so, same is set to be equal to S, and the time of occurrence of the minimum tMIN is set to be equal to the actual time at S7. Thereafter, it is examined at S8 whether the first derivative is smaller than the value indicative of the maximum absolute value of the first derivative DMIN1. If so, DMIN1 is set to be equal to the actual first derivative (S9). The time of occurrence thereof tDMIN1 is set to equal the actual time at S10. Thereafter the routine goes to S5.

If the condition at S6 is not fulfilled, a flag "edge complete" is set (S11) before the software routine in accordance with FIG. 6 is left.

Figure 7:
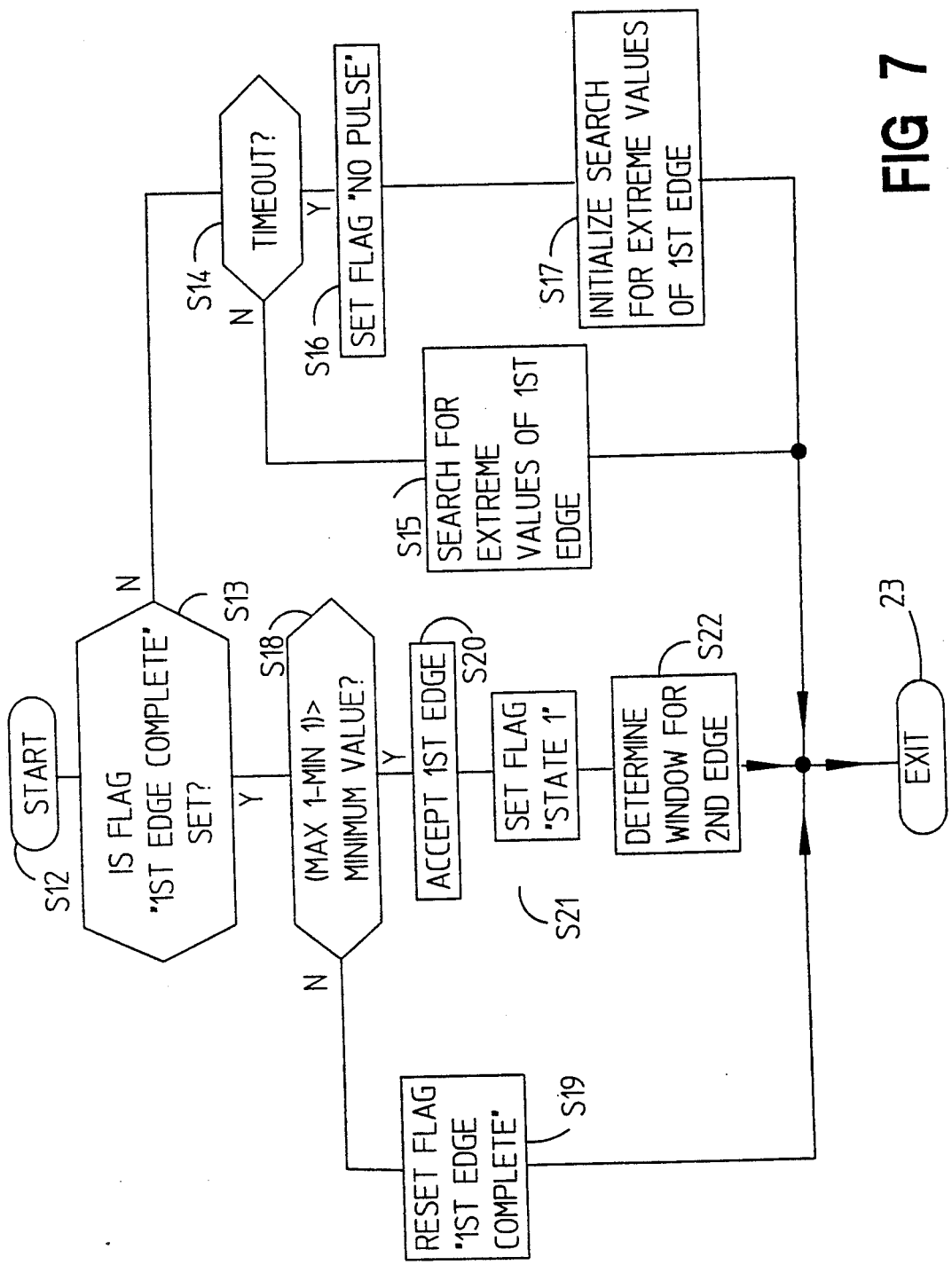
FIG. 7 shows a flow diagram of the signal analysis as carried out in the first constitution.

As depicted in FIG. 7, after entering the routine at S12, it is examined at step S13 whether the flag "first edge complete" is set.

If this condition is not fulfilled, it is examined at step S14 whether a time threshold TIMEOUT is exceeded. If this condition is not fulfilled, a search for extreme values e.g. the maximum and minimum of the first edge is conducted at step S15 before leaving this routine.

Otherwise at S16 a flag "no pulse" is set for indicating that an inadmissible time period lapsed due to certain errors in operating the oximeter system. Subsequently, the search for extreme values of the first edge is initialized at step S17 before leaving the routine.

If it is determined at S13 that the flag "first edge complete" is set, it is subsequently examined at S18 whether the difference between the extreme values (MAX1−MIN1) exceeds a predetermined threshold or minimum value for restarting the search as the firstly detected edge is to be regarded as a noise, a small dicrotic pulse or a minimal artifact. If this condition is not fulfilled, the flag "first edge complete" is reset at step S19 before leaving the routine at step S23 for repeating the routine indicated in FIG. 6.

If the reply to the examination under step S18 is affirmative, the detected first edge is accepted at S20, a flag "state 2"is set at S21 and a window for the expected second edge is determined or calculated at step S22 before leaving the routine at S23.

Figure 9:
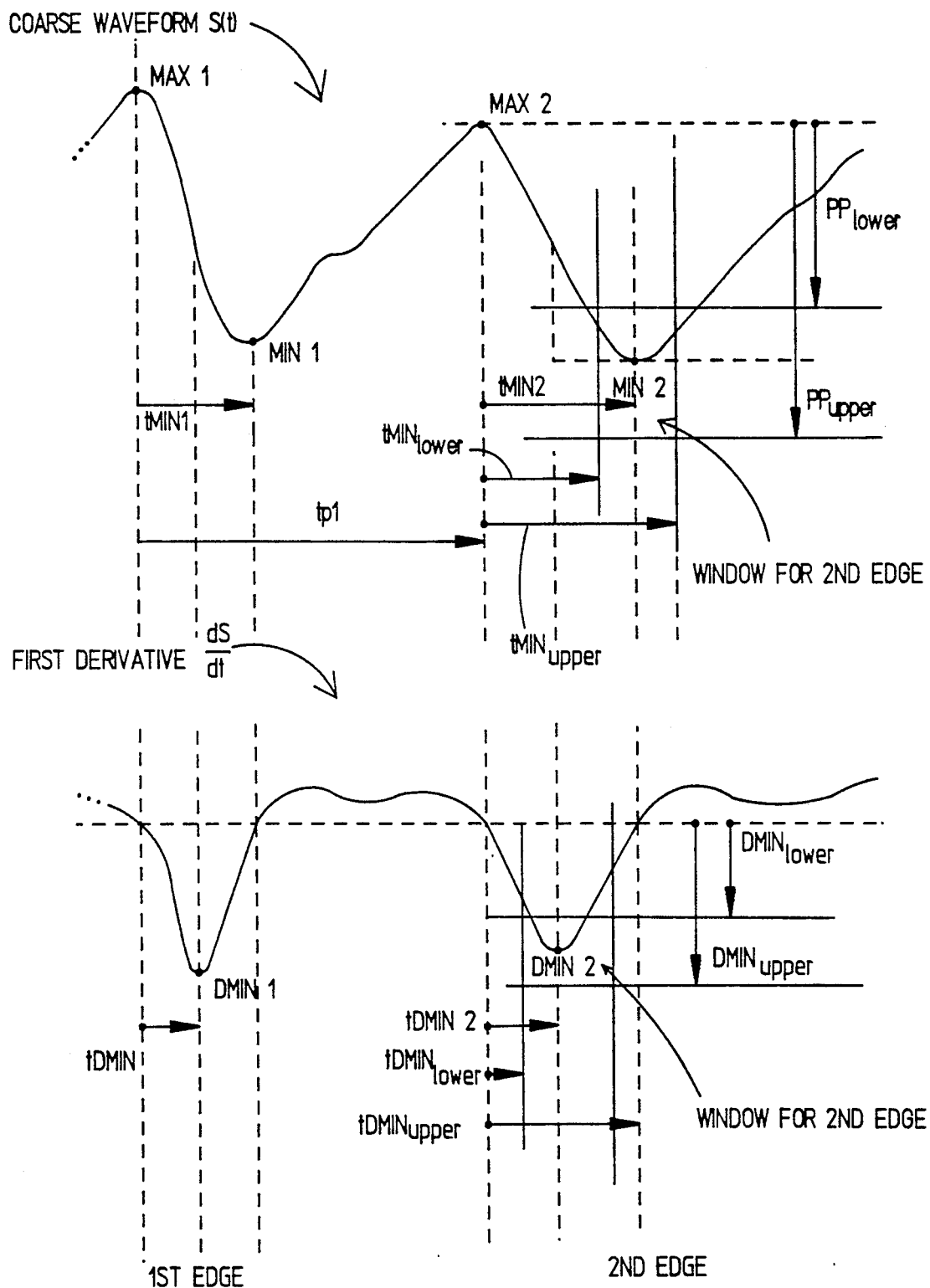
FIG. 9 shows a graph essentially corresponding to the one of FIG. 4, including a representation of the window used for the search for the second edge of the signal.

The window is defined based on characteristic features of the first edge. As shown in FIG. 9, the window for the second edge is defined by an admissible range for the amplitude of the second edge, for the period thereof, for the maximum absolute value of the first derivative and for the time between the maximum and the maximum value of the first derivative.

In other words, the window is defined as follows:

$$PP\_upper = a * (MAX1-MIN1), a > 1,$$

$$PP\_lower = b * (MAX1-MIN1), b = 0 \ldots 1;$$

$$tMIN\_upper = c * tMIN1, c > 1,$$

$$tMIN\_lower = d * tMIN1, d = 0 \ldots 1;$$

$$DMIN\_upper = e * DMIN1, e > 1,$$

$$DMIN\_lower = f * DMIN1, f = 0 \ldots 1;$$

$$tDMIN\_upper = g * tDMIN1, g > 1, and$$

$$tDMIN\_lower = h * tDMIN1, h = 0 \ldots 1.$$

The values a, b, c, d, e, f, g and h are empirically determined constants taking into account physiological pulse-to-pulse variation of the systolic edge.

PP_upper and PP_lower are upper and lower thresholds for the amplitude of the edge, e.g. for the difference between MAX2 and an expected MIN2. tMIN_upper and tMIN_lower are upper and lower threshold values for the period or end of the edge. DMIN_upper and DMIN_lower are upper and lower threshold values for an admissible range of the absolute maximum value of the first derivative. tDMIN_upper and tDMIN_lower are upper and lower threshold values for the time periods between the second maximum MAX2 and the occurrence of the absolute maximum value of the first derivative DMIN2.

FIG. 8 (a,b) is a software routine corresponding to state 2 shown in FIG. 5.

Figure 8A:
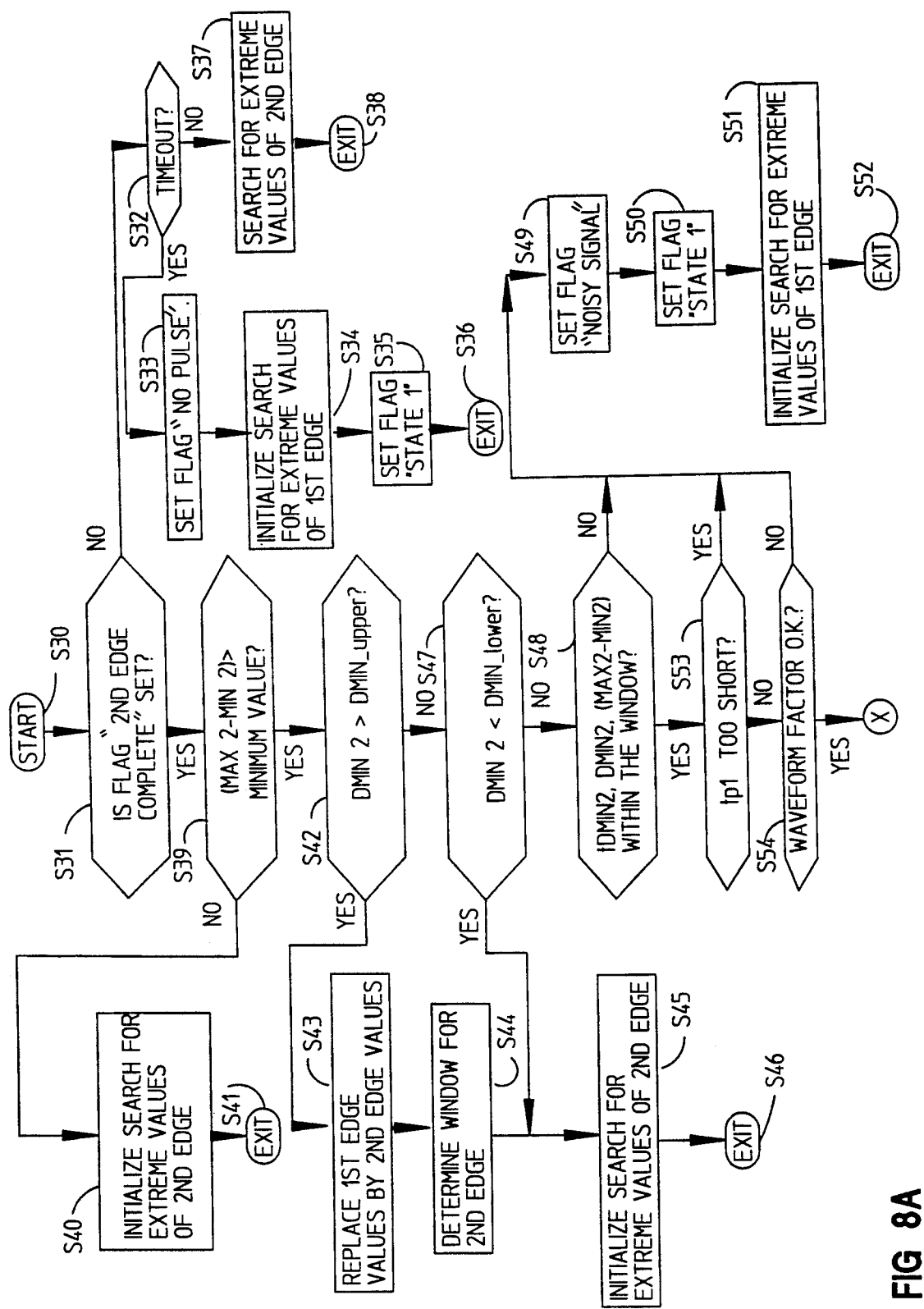
FIGS. 8a, 8b depict a flow diagram of the search for a second edge of the signal, for evaluating same and for storing certain values or characteristics of the accepted second edge for the purpose of a further calculation based thereon.
Figure 8B:
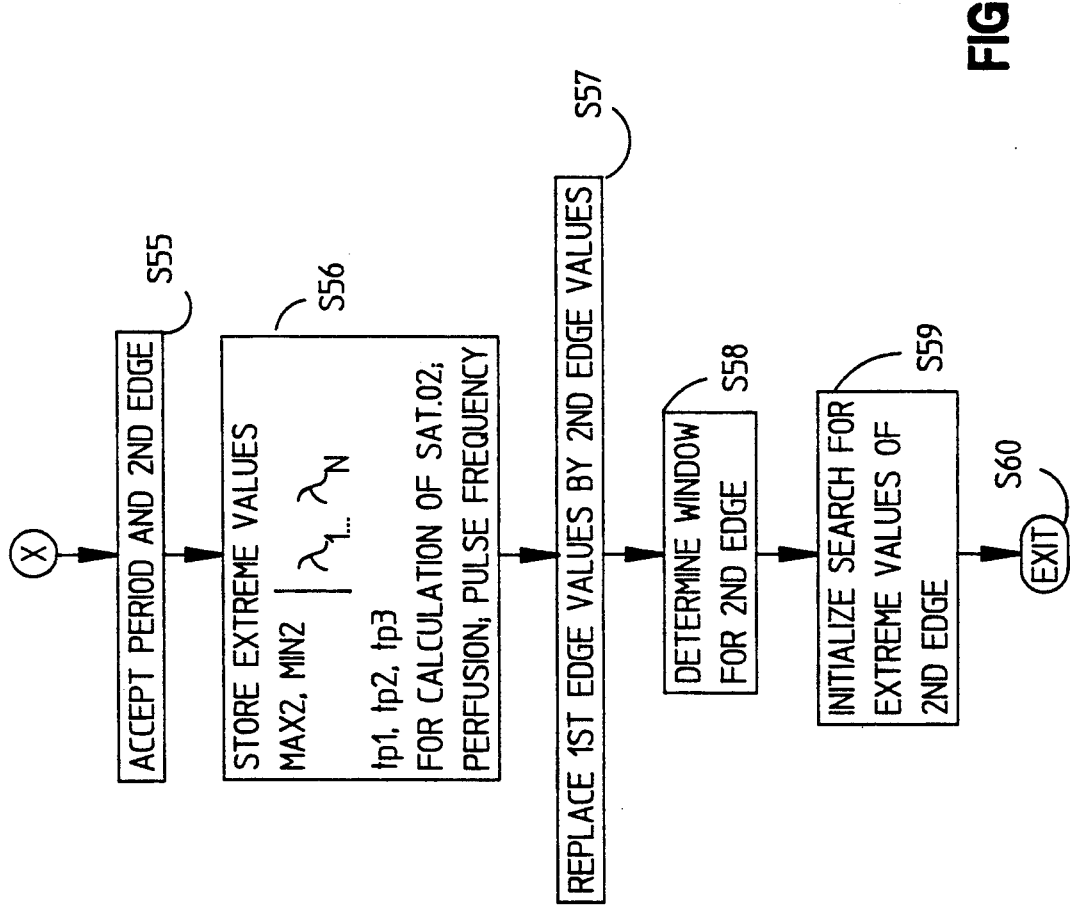

After entering the routine (S30), it is examined at S31 whether the flag "second edge complete" is set. FIG. 8A to determine whether or not the second edge has passed through the windows. FIG. 7 is only used for selecting the first edge. The parameters of the second edge necessary to determine whether or not the second edge meets the conditions for the four windows defined above and illustrated in FIG. 9 are determined by the procedures of FIG. 6. These parameters are used in FIG. 8A. If this condition is not fulfilled, it is examined at S32 whether a time threshold (TIMEOUT) is exceeded before the occurrence of further edge. If this condition is fulfilled, a flag "no pulse" is set at step S33, the search for extreme values of the first edge is initialized at step S34, the flag "state 1"is set at step S35, before leaving the routine at S36 and returning to the flow diagram of FIG. 6.

If the condition in accordance with S32 is not fulfilled, the search for extreme values (MIN2, MAX2, DMIN2) of the second edge is continued at S37 before leaving the routine at S38.

If it is confirmed at S31 that the flag "second edge complete" is set, the amplitude (MAX2-MIN2) is compared to a minimum value at S39. If it does not exceed same, the search for extreme values of the second edge is initialized at S40 before leaving the routine at S41. Otherwise, it is examined whether the absolute maximum value of the first derivative of the second edge DMIN2 exceeds the upper threshold DMIN_upper at S42.

If so, the first edge will be disregarded by replacing the characteristic values of the previously detected first edge by the actual values of the second edge at S43. This step serves for selecting the edge having the greatest first derivative as a reference value for making certain that artifacts or dicrotic values do not form the reference edge.

A window is again defined at S44 before once more initializing the search for extreme values of the second edge at S45 and subsequently leaving the routine at S46.

If the condition in accordance with step S42 is not fulfilled, it is examined whether the maximum absolute value of the first derivative is smaller than the lower threshold value DMIN_lower at S47. If so, the program proceeds to S45, otherwise it is examined at S48 whether tDMIN2, tMIN2 and (MAX2-MIN2) fall within the window. If this condition in accordance with step S48 is not fulfilled, the flag "noisy signal" is set at S49, the flag "state 1" is set at S50 before initializing the search for extreme values of the first edge at S51 and leaving this routine at S52.

If the condition of step S48 is fulfilled, it is examined whether the period tp1 is shorter than a value corresponding to the upper threshold of the pulse frequency at S53. If so, the program proceeds to S49, otherwise it proceeds to S54 where the so-called waveform factor defined by the ratio tMIN2/tp1 is checked. If the waveform factor is not within a reasonable range, the program proceeds to S49, otherwise it proceeds to S55 (FIG. 8(b)). At S55 the period and second edge are accepted. At S56 the extreme values MAX2, MIN2 for the respective wavelengths, the respective periods tp1, tp2, tp3 (periods between the respective extreme values MAX, MIN, DMIN) are stored.

Subsequently, the oxygen saturation is calculated by firstly determining the following RATIO:

$$RATIO = \frac{\ln(MAX2(lambda1)/MIN2(lambda1))}{\ln(MAX2(lambda2)/MIN2(lambda2))}$$

Having determined the above-defined RATIO, the oxyhemoglobin saturation SaO2 is determined on the basis of an empirically defined correlation which is stored in a read-only-memory:

SaO2=F(RATIO).

Thereinafter, the pulse frequency PR is derived as follows:

$$PR\ (bpm) = \frac{180}{tp1 + tp2 + tp3\ (s)}$$

At S57 the characteristic values of the actual first edge are replaced by those of the actual second one for updating the first edge. A further updated window for the second edge is then defined at S58. Subsequently, the search for extreme values of the second edge is initialized again at S59 before leaving the routine at S60.

What is claimed is:

1. Apparatus for processing a signal of varying amplitude so as to detect systolic edges comprising:
   first means for determining if edges in the signal have a MAX1 and MIN1;
   second means for determining the maximum absolute value DMIN of the first derivative of edges having MAX1 and MIN1;
   third means for determining the time tMIN1 between MAX1 and MIN1;
   fourth means for determining the time tDMIN1 between MAX1 and the occurrence of DMIN;
   means for accepting an edge as a first edge if MAX1−MIN1> a given value and for determining the MAX1 and MIN1 of a subsequent edge if MAX1-MIN1 is not > said given value;
   means for defining the following upper and lower values of windows, PP_upper = a (MAX1-MIN1), where a > 1, PP_lower = b (MAX1-MIN1), where b = 0 . . . 1, tMIN_upper = c (tMIN1), where c > 1, tMIN_lower = d (tMIN1), where d = 0 . . . 1, DMIN_upper = e (DMIN1), where e > 1, DMIN_lower = f (DMIN1), where f = 0 . . . 1, tDMIN_lower = g (tDMIN1), where g > 1, tDMIN_upper = h (tDMIN1), where h = 0 . . . 1, means for determining if a second edge has been subjected to the operation of the first through the fourth means so as to derive MAX2, MIN2, tMIN2 and tDMIN2;
   means for determining if the second edge has values within said windows; and
   means for storing the values MAX2 and MIN2 if the second edge has values within said windows.

2. Apparatus for processing a signal for arterial blood flow so as to identify systolic edges more reliably comprising:

means for identifying a portion of said signal as a first systolic edge when it meets given criteria;

means for determining the maximum value of the first derivative of the portion of the signal in said first systolic edge;

means for determining the time of occurrence of the maximum value of said first derivative relative to one end of said first systolic edge;

means responsive to said time of occurrence for deriving a range of times of occurrence for the maximum value of the first derivative;

means for providing an indication when a later portion of said signal meets given criteria for a potential second systolic edge;

means for determining the maximum value of the first derivative in the signal in said potential second systolic edge;

means for determining the time of occurrence of said latter maximum value of the first derivative relative to one end of said potential second systolic edge; and means for providing further indication that the potential second systolic edge is a true systolic edge if the time of occurrence of the maximum value of its first derivative falls within said range.

3. A method for processing a signal corresponding to arterial blood flow so as to identify systolic edges more reliably comprising:

identifying a portion of the signal as a potential first systolic edge when it meets certain criteria;

deriving the first derivative of the portion of the signal in said first systolic edge;

determining the maximum value of said first derivative;

determining the time of occurrence of said maximum value of said first derivative with respect to one end of said first systolic edge;

deriving a range of times of occurrence of a maximum value of a first derivative in response to at least the time of occurrence of the maximum value of the first derivative in said first systolic edge;

providing an indication when a later portion of said signal meets given criteria for a potential second systolic edge; and providing further indication that the second systolic edge is a true systolic edge when the time of occurrence of the maximum value of its first derivative with respect to an end thereof falls within said range.

* * * * *